United States Patent
Frame et al.

(10) Patent No.: US 11,284,499 B2
(45) Date of Patent: *Mar. 22, 2022

(54) WOUND DRESSING

(71) Applicant: FOURTH STATE MEDICINE LTD., Heslemere (GB)

(72) Inventors: Thomas E D Frame, Hampshire (GB); Thomas Harle, Essex (GB); Thomas Wantock, Godalming (GB)

(73) Assignee: FOURTH STATE MEDICINE LTD., Heslemere (GB)

( * ) Notice: Subject to any disclaimer, the term of this patent is extended or adjusted under 35 U.S.C. 154(b) by 308 days.

This patent is subject to a terminal disclaimer.

(21) Appl. No.: 16/085,403

(22) PCT Filed: Mar. 16, 2017

(86) PCT No.: PCT/GB2017/050734
§ 371 (c)(1),
(2) Date: Sep. 14, 2018

(87) PCT Pub. No.: WO2017/158369
PCT Pub. Date: Sep. 21, 2017

(65) Prior Publication Data
US 2019/0098738 A1    Mar. 28, 2019

(30) Foreign Application Priority Data

Mar. 16, 2016  (GB) ...................................... 1604489

(51) Int. Cl.
*H05H 1/24* (2006.01)
*H05H 1/34* (2006.01)
(Continued)

(52) U.S. Cl.
CPC .......... *H05H 1/2406* (2013.01); *A61L 2/007* (2013.01); *A61L 2/0011* (2013.01); *A61L 2/14* (2013.01);
(Continued)

(58) Field of Classification Search
CPC .. H05H 1/2406; H05H 1/34; H05H 2245/122; H05H 2277/10;
(Continued)

(56) References Cited

U.S. PATENT DOCUMENTS 10,595,391 B2 * 3/2020 Knoll ................... A61N 1/0424
2003/0069576 A1 * 4/2003 Tanrisever ............... H05H 1/48
606/41

(Continued)

FOREIGN PATENT DOCUMENTS

CN   101052365 A   10/2007
CN   101652016 A   2/2010
(Continued)

OTHER PUBLICATIONS

First Office Action in corresponding Chinese Patent Application No. 201780030142.4 dated Jun. 3, 2020.

*Primary Examiner* — Xiuyu Tai
(74) *Attorney, Agent, or Firm* — Lando & Anastasi, LLP

(57) ABSTRACT

A kit of parts for use in treatment of tissue by a contained plasma and/or plasma products is disclosed. The kit of parts includes a plasma generating device for use with a membrane dressing attached to tissue requiring treatment. The plasma generating device comprises a first cavity with an opening at one end formed between a grounded electrode and a cathode such that, in use, an arc discharge between the cathode and the grounded electrode ionizes a feed gas to produce at the open end a thermal plasma. Furthermore, the
(Continued)

plasma generating device also comprises a second cavity with an opening at one end formed between a high voltage electrode and a grounded electrode such that, in use, a dielectric barrier discharge between the high voltage electrode and grounded electrode ionizes a feed gas to produce at the open end a non-thermal plasma. The membrane dressing is suitable for covering tissue in use, such as a diabetic ulcer, and comprises a sheet of impermeable material configured for forming a plasma containment compartment adjacent to the tissue. The membrane dressing also comprises one or more input connectors configured to admit plasma and/or plasma products through the membrane dressing. The plasma generating device and the one or more input convectors of the membrane dressing are configured to allow the plasma generating device and the input connector to be directly coupled or indirectly coupled through a connector tube to allow fluid communication of the plasma and/or plasma products produced at the openings of the cavities of the plasma generating device through the membrane dressing to, in use, allow conduction of the produced plasma into the membrane dressing. Advantages of such a kit of parts may be that the membrane dressing does not need to be removed to inspect the progress of the wound, nor does it need to be removed and replaced to manage the exudate. Such advantages helps to mitigate the problems of wound aggravation and maceration typically associated with well-known wound dressings, and also helps to encourage and facilitate wound healing.

11 Claims, 3 Drawing Sheets

(51) Int. Cl.
*A61L 2/00* (2006.01)
*A61L 2/14* (2006.01)
*A61F 13/00* (2006.01)
*A61N 1/04* (2006.01)

(52) U.S. Cl.
CPC ......... *H05H 1/34* (2013.01); *A61F 13/00051* (2013.01); *A61N 1/0468* (2013.01); *H05H 2245/30* (2021.05)

(58) Field of Classification Search
CPC ............. H05H 2001/3447; H05H 1/48; H05H 2201/483; H05H 1/42; H05H 2001/3484; H05H 2245/30; H05H 1/471; A61L 2/0011; A61L 2/007; A61L 2/14; A61L 2202/11; A61F 13/00051; A61N 1/0468; A61N 1/44; A61N 1/0472; A61N 1/042; A61B 18/042; A61B 2018/00577; A61B 2018/0047; C01B 33/037
See application file for complete search history.

(56) References Cited

U.S. PATENT DOCUMENTS

| | | |
|---|---|---|
| 2005/0236374 A1 | 10/2005 | Blankenship |
| 2012/0046602 A1* | 2/2012 | Morfill ................. A61M 35/00 604/23 |
| 2012/0296265 A1 | 11/2012 | Dobrynin et al. |
| 2013/0158337 A1 | 6/2013 | Okano |
| 2015/0004361 A1 | 1/2015 | Culpepper |
| 2017/0354453 A1* | 12/2017 | Krasik .................. A61B 1/018 |
| 2019/0090339 A1* | 3/2019 | Frame ................... A61L 2/0011 |

FOREIGN PATENT DOCUMENTS

| | | |
|---|---|---|
| CN | 103079639 A | 5/2013 |
| CN | 104869953 A | 8/2015 |
| DE | 202008018264 U1 | 7/2012 |
| EP | 2338447 A1 | 6/2011 |
| WO | 2010034451 A1 | 4/2010 |
| WO | 2010034451 A8 | 6/2010 |
| WO | 2015/008191 A1 | 1/2015 |
| WO | 2015087278 A1 | 6/2015 |
| WO | 2017158369 A1 | 9/2017 |

* cited by examiner

WOUND DRESSING

CROSS-REFERENCE TO RELATED APPLICATIONS

This application is a U.S. National Phase Application under 35 U.S.C. § 371 of International Application No. PCT/GB2017/050734 filed Mar. 16, 2017, which claims priority to Great Britain Application No. 1604489.3 filed Mar. 16, 2016.

FIELD OF THE TECHNOLOGY

The present invention relates generally to wound dressings, and to a kit of parts for use in treatment of tissue by a contained plasma and/or plasma products, the contained plasma and/or plasma products providing the wound dressing in use.

In particular, the present invention relates to membranes, plasma generating devices, electrical power generator unit and methods of operation thereof for generating and containing a plasma plume having a thermal plasma and a non-thermal plasma and associated plasma products. The wound dressing finds particular utility in the healing and sterilisation of diabetic ulcers.

BACKGROUND

Wound management and treatment is a highly complex field. Typically wounds are managed and treated using dressings, of which there are many different types. The type of dressing used will usually depending on the severity and other characteristics of the wound, such as the amount of exudate produced.

Wounds normally heal in three phases: inflammatory, proliferation and maturation. The inflammatory phase is defined by blood clots forming in the wound to stop the bleeding. At this stage, the blood vessels surrounding the wound dilate and allow cells such as antibodies and white blood cells to reach the wound, which naturally leads to an increase in exudate produced from the wound. The proliferation phase is where granulation tissue forms at the base of the wound, and eventually fills the wound. Finally, maturation involves the restructuring of collagen to increase the tensile strength of the wound, such that the scar tissue is around 80% as strong as normal "healthy" tissue.

Wound dressings are normally used to protect the wound during the three phases of healing, particularly during the inflammatory and proliferation phases. Any interruption or delay of these phases could result in a delay in the overall healing process, or lead to a non-healing chronic wound such as an ulcer. As well as protecting the wound, dressings also aim to alleviate symptoms such as pain and bleeding, encourage healing and reduce the risk of infection. The common types of dressings used in wound management include Hydrocolloid, Hydrogel, Alginate and Foam.

Hydrocolloid dressings are non-breathable, waterproof and adhesive with an active surface coated with, inter alia, gelatin, pectin, and other adhesives. Any exudate is absorbed by the active surface and reacts with the active coating to form a gel which is held within the structure of the adhesives. Due to the waterproof nature of hydrocolloid dressings, they are impermeable to bacteria and so the risk of the wound becoming infected is minimised.

Hydrogel dressings are 90% water and comprise a gel base with a three-dimensional network of hydrophilic polymers which can absorb exudate produced from the wound. The gel base also provides a cooling effect which can assist with pain management. The hydrogel dressing also regulates the amount of moisture at the wound surface, such as by donating or absorbing moisture from the wound in order to keep the wound surface moist, but not overly so, as too much or too little moisture can lead to complications in the healing process.

Alginate dressings are derived from seaweed and are very absorbent due to the high number of biodegradable fibres naturally present. These dressings are suitable for wounds producing a large volume of exudate, as the naturally occurring fibres are very absorbent.

Foam dressings are also very absorbent and are thus applicable on a wide range of wounds with heavy exudate production. They can be cut to fit in and around irregularly shaped wounds to provide ample cushioning and protection of the healing wound.

Despite the benefits of using dressings in wound management, they also have significant drawbacks. For example, some dressings can cause maceration of the skin surrounding the wound, which is where moisture gets trapped against the skin for prolonged periods of time and over-hydrates the skin. Maceration can be caused by inadequate exudate management where a dressing is used that is unable to handle the amount of exudate produced from the wound, or if a dressing is not changed frequently enough. This problem is common with hydrogel dressings due to the amount of moisture present.

All dressings require frequent changing for wound inspection, and also to help reduce the maceration of the surrounding skin. Changing the dressing too frequently however can aggravate the wound which can result in a prolonged healing time. This is common with hydrocolloid dressings where the adhesive dressing can adhere to the wound and cause damage to the wound when the dressing is removed. This can also occur with foam dressings which are ineffective at regulating the moisture levels at the wound, such that maceration of the skin surrounding the wound can occur if more exudate is produced than the dressing can cope with, or the wound can dry out if little or no exudate is produced. If the dressing and/or the wound dries out, the foam dressing can stick to the wound and the surrounding skin, such that when the dressing is removed, it can cause damage to the wound, particularly any newly formed tissue (granulation tissue), and this can cause the patient much pain and distress. Frequent changing of the dressing can also lead to the problem of skin stripping, where the repeated application and removal of the adhesive part of the dressing can damage the outermost layer of the skin.

An alternative method for managing and treating wounds is Negative-Pressure Wound Therapy (NPWT), which has been shown to improve wound healing. The method includes cutting a dressing, typically a foam dressing, to the size of the wound and using it to fill the wound before a thin transparent film is applied over the top to create a seal around the wound and the dressing. A vacuum pump is then attached to an opening in the film. Activating the vacuum pump creates a negative pressure within the sealed film, which helps to remove exudate from the wound where it is subsequently absorbed by the dressing. There are drawbacks to this method however, and these include the initial drop in pressure causing the patient pain and discomfort. The dressing also needs to be removed and changed frequently which increases the risk of skin stripping and aggravating the wound, thus prolonging healing time and counteracting any improvements made in the healing process.

A further method for helping to treat wounds is applying silver to the wound or to the part of the dressing covering the wound. Silver is often used due to its antibacterial and anti-inflammatory properties which are thought to help to minimise infections and speed up healing time. Silver has also been shown to reduce the frequency which some dressings need changed, thus helping to minimise the damage caused to wounds and the surrounding tissue when the dressing is eventually removed or changed. There are concerns however that prolonged use of silver dressings can lead to argyria, or discoloration of the skin, which is irreversible. There are also some concerns about the toxicity of silver, and the potential build-up of silver in the body when silver dressings are used over a prolonged period of time.

Certain conditions, such as diabetes, can disrupt the wound healing process, leading to significantly delayed or impaired ability to heal wounds. In this instance, a prolonged inflammatory phase occurs, which delays the formation of mature granulation tissue, leading to an open wound an reduced wound tensile strength. Diabetic wounds or ulcers can thus require longer term wound management in order to facilitate their effective repair, to avoid them becoming a chronic condition. However, many of the traditional approaches to dressing wounds disrupt and set back the slow process of wound recovery in diabetics. Wounds left open for extended periods of time may become infected, which can lead to amputations becoming necessary.

In view of the above, there is an interest in developing new wound dressings, and methods of treating wounds, which promote the healing of wounds as well as mitigating one or more of the above problems. It is in this context that the present invention is devised.

SUMMARY

Viewed from one aspect, the present invention provides a kit of parts for use in treatment of tissue by a contained plasma and/or plasma products, comprising:
  a plasma generating device for use with a membrane dressing attached to tissue requiring treatment, comprising:
    a first cavity with an opening at one end formed between a grounded electrode and a cathode such that, in use, an arc discharge between the cathode and the grounded electrode ionizes a feed gas to produce at the open end a thermal plasma and plasma products; and
    a second cavity with an opening at one end formed between a high voltage electrode and a grounded electrode such that, in use, a dielectric barrier discharge between the high voltage electrode and grounded electrode ionizes a feed gas to produce at the open end a non-thermal plasma and plasma products; and
  a membrane dressing for covering a tissue in use, the membrane dressing comprising:
    a sheet of impermeable material configured for forming a plasma containment compartment adjacent tissue; and
    one or more input connectors configured to admit plasma and/or plasma products through the membrane dressing;
  wherein the plasma generating device and the one or more input connectors of the membrane dressing are configured to allow the plasma generating device and the input connector to be directly coupled or indirectly coupled through a connector tube to allow fluid communication of the plasma and/or plasma products produced at the openings of the cavities of the plasma generating device through the membrane dressing to, in use, allow conduction of the produced plasma and/or plasma products into the membrane dressing. In embodiments, the high voltage electrode may comprise a dielectric barrier material. In embodiments, the sheet of impermeable material configured for forming a plasma containment compartment adjacent tissue, may be configured such that, when faced against a tissue, a tissue-facing inner surface of the impermeable material defines a sealed environment which prevents plasma and/or plasma products from escaping to a surrounding environment.

In accordance with the present invention, a plasma treatment is provided that has a wide range of utility. For example, a plasma procedure is provided wherein a two-stage plasma is produced which interacts to form plasma products, the plasma and/or plasma products are injected through a membrane dressing sealed around a wound, such as a diabetic ulcer. The two-stage plasma comprises a lower energy non-thermal plasma and a higher energy thermal plasma.

In embodiments, the interaction between the thermal and non-thermal plasma produces various plasma products, such as free radicals. The concentrations of these radicals produced can be varied by manipulating the parameters of both the thermal and non-thermal plasma, for example the power and the flow rate. Compared to plasma sources that use only one type of plasma, the interaction between the thermal and non-thermal plasmas will produce different concentrations of radicals which allows a wider range of utility of the present invention.

The lower energy non-thermal plasma provides free radicals, for example Nitric Oxide and/or Ozone, which has a sterilizing effect on the wound and may help to speed up the healing process; whereas the higher energy thermal plasma provides ultraviolet radiation which may also act to sterilize the wound and encourage rejuvenation and regeneration of tissue. The higher energy plasma also provides heat which may assist with thermally stimulating, mixing and convecting the free radicals around the wound to facilitate healing thereof.

In embodiments, the volume of plasma product, such as free radicals, contained within the membrane dressing is greater than the volume of two-stage plasma contained within the membrane dressing. In embodiments, only plasma products will be contained within the membrane dressing.

The two-stage plasma and/or plasma products contained within the membrane dressing, particularly within the plasma containment compartment, remains in situ for the duration of the treatment. After the treatment duration, the plasma gas, which includes the plasma products, and any exudate secreted from the wound, may be removed from the sealed environment of the plasma containment compartment; subsequently if further treatment is required, more plasma and/or plasma products may be generated and injected through the membrane into the plasma containment compartment. Leaving the plasma and/or plasma product in situ for the duration of the treatment may facilitate the healing of the wound, and may also help to reduce recovery times. In addition, a reduced recovery period may allow the procedure to be carried out by trained, non-medical personnel in a non-surgical setting.

In embodiments, the membrane dressing is at least partly transparent to allow viewing of the tissue during treatment. Such transparency means that the membrane dressing may not need to be removed at any time during the healing process to check the progress of the wound, thus avoiding aggravating the wound and surrounding skin.

In embodiments, the membrane dressing further comprises an outer surface and a tissue-facing inner surface which surrounds a plasma containment compartment, or cavity. The membrane dressing is impermeable, thus the tissue-facing inner surface defines a sealed environment which prevents plasma and/or plasma products from escaping to the surrounding environment, and also prevents bacteria from the surrounding environment infecting the wound. The sealed environment also allows the possibility of controlling parameters such as temperature and humidity, and any other parameters which are relevant to wound care. An outer portion of the tissue-facing inner surface has an adhesive layer for attaching and sealing, in use, the membrane dressing over and around the wound. The adhesive may be, for example, a compound tincture of benzoin.

In embodiments, at least a plasma containment compartment of the membrane dressing is formed to protrude from an outer portion of the membrane dressing as a blister or dome shape, or is configured to form a blister-shape or dome-shape in use, such that the plasma containment compartment of the membrane dressing in use extends away from and is spaced apart from the wound. That is a centre portion of the membrane dressing extends longitudinally further than the outer portion of the membrane dressing. In use, the center portion of the membrane dressing sits over but does not touch the wound, thus in cases where the membrane dressing needs to be removed, the membrane dressing may not aggravate the wound and prolong the healing time thereof.

In embodiments, there are a selection of membrane dressings having different shapes and sizes for the treatment different sized wounds.

In embodiments, the membrane dressing further comprises one or more exit connectors configured to, in use, allow exudate and/or plasma gas to issue therethrough through the membrane dressing, optionally to a waste container connected thereto. In embodiments, one or more of the exit connectors is integrated with and optionally cooperates with one or more of the input connectors. In embodiments, the exit connector is located off centre, longitudinally between the centre portion and the outer portion of the membrane dressing. In use, the input connector and the exit connector maintain the seal created by the membrane dressing.

In embodiments, the plasma generating device is configured such that the second cavity is arranged around the first cavity, wherein:
the cathode of the first cavity is provided as a central cathode rod;
wherein the grounded electrode of the first and second cavities is provided as a grounded conductive tube arranged around the cathode rod and spaced therefrom to form the first cavity as a cylinder having said opening at one end thereof; and wherein the a high voltage electrode of the second cavity is provided around the grounded conductive tube and spaced apart therefrom to form the second cavity as an annular cylinder having said opening at one end thereof, the high voltage electrode having a dielectric barrier material at a radially inward-facing surface thereof;

In embodiments, the cathode, grounded electrode and high voltage electrode are arranged co-axially. In embodiments, the end of the central cathode rod is recessed from an open end of the grounded tube.

In embodiments, the plasma generating device further comprises at least one feed gas connector for connecting each of the first and second cavities to a feed gas supply and electrical connectors coupled to the connecting the cathode rod, grounded tube and the high voltage electrode; wherein one or more of the feed gas connectors and/or one or more of the electrical connectors is arranged at a 90 degree angle to the major axis of the cathode rod, grounded tube and the high voltage electrode. Such a configuration provides a compact apparatus which can fit into a flattened handheld device, thus making the plasma generating device more portable. The flattened handheld device also allows the routing of wires parallel to the patient's skin, thus reducing the likelihood of catching protruding wires and tugging on the dressing when moving around, resulting in improved patient comfort.

In embodiments, the plasma generating device is dimensioned generally to be relatively short in the axis in which the plasma issues from the device, and relatively large in at least one orthogonal axis, wherein optionally the plasma generating device is shaped as a puck. The treatment is typically non-invasive and poses minimal health risks and side effects, the kit of parts in accordance with the aspects and embodiments of the invention described herein could be used by appropriately trained, non-medical personnel in a non-medical setting.

In embodiments, the plasma generating device further comprises at least one connector for coupling, in use, an opening of the plasma generating device through which plasma and/or plasma product issues to an input connector of the membrane dressing or connector tube, or wherein the plasma generating device is formed such that an opening of the plasma generating device through which plasma and/or plasma product issues is coupleable to an input connector of the membrane dressing or connector tube. In embodiments, the input connector is located in the centre portion of the membrane dressing. In embodiments, the input connector may be located away from the centre portion.

In embodiments, the plasma generating device further comprises at least one feed gas inlet opening for each of the first and second cavities; wherein the kit of parts in accordance with the aspects and embodiments of the invention described herein is configured to provide sealed fluid communication between each feed gas inlet and the input connector of the membrane dressing.

In embodiments, the apparatus further comprises one or more containers of feed gas connected to the plasma generating device, wherein the apparatus is configured such that feed gas is supplied to the first and second cavities to be ionized in use. In embodiments, the kit of parts in accordance with the aspects and embodiments of the invention described herein is configured to provide sealed fluid communication between each feed gas inlet and a feed gas connector for connecting to a feed gas supply.

In embodiments, separate feed gas connectors are provided for each of the first and second cavities, and wherein the plasma generating device is further configured such that fluid communication lines between the feed gas connectors and the feed gas inlets to the first and second cavities are sealed from each other, such that separate feed gases are in use supplied to the first and second cavities.

In embodiments, the kit of parts in accordance with the aspects and embodiments of the invention described herein also comprises an electrical power generator unit for coupling to the plasma generating device, the electrical power generator unit comprising:

means configured to provide to the cathode in use a constant direct current (DC) electrical power supply plus a high voltage pulsed electrical power supply to initiate the arc discharge in the first cavity; and means configured to provide to the high voltage electrode in use a high voltage alternating current electrical power supply or pulsed electrical power supply to generate the dielectric barrier discharge in the second annular cavity.

In embodiments, the plasma generating device further comprises a connector which, in use, couples the plasma generating device to an electrical power generator unit.

In embodiments, the plasma generating device further comprises a battery power supply either provided separately to or as part of the plasma generating device which, in use, makes the plasma generating device portable and easily operated outside of a medical setting by non-medical personnel.

In use, a constant direct current (DC) electrical power plus a high voltage pulsed electrical power is provided to the cathode producing an arc discharge in the first cavity between the cathode and grounded tube to generate a central thermal plasma emitted at an open end of the first cylindrical cavity. Also, in use, a high voltage alternating current electrical power or pulsed electrical power is provided to the high voltage electrode producing a dielectric barrier discharge in the second annular cylindrical cavity to generate a non-thermal plasma emitted from an open end of the second cavity.

In preferred embodiments, the behaviour of the thermal plasma is dominated by fluid dynamics. The arc discharge acts as an intense source of heat and ionisation which is propagated in use towards the open end of the torch by the flowing feed gas. In this way, the thermal plasma is also guided towards the open end of the torch where it is then emitted. The emission of the thermal plasma may however be interrupted by the one or more input connectors or the connector tube indirectly coupling the plasma generating device to the membrane dressing, such that the thermal plasma, along with the non-thermal plasma emitted from the open end of the second cavity and/or any thermal and non-thermal plasma products, is injected through the membrane dressing and into the plasma containment compartment.

In embodiments, the fluence and energy distribution of the thermal plasma can be controlled by manipulating the location and properties of the arc and the flow of the feed gas.

In other embodiments, the end of the central cathode rod is recessed from an open end of the grounded tube such that, in use, the arc current causes a Lorentz force that accelerates the thermal plasma towards a focal point in front of the open end of the plasma generating device. The arrangement of the electrodes in this way causes a magnetic field generated in the first cavity by the current travelling through the grounded tube and the cathode (due to the arc discharge therebetween), with magnetic field lines flowing cylindrically around the cathode. This magnetic field itself has an effect on the charged thermal plasma generated by the arc discharge of producing a Lorentz force on the plasma, which, due to the recess of the cathode compared to the open end of the grounded tube, is directed towards the central common axis of the electrodes in front of the open end of the grounded tube. In this way, the thermal plasma experiences an acceleration towards a focal point in front of the open end of the torch. In different embodiments, the effect of this magnetic field on focussing the thermal plasma is more or less significant, although in embodiments it can be less significant than the thermal effects of convection of the plasma. In embodiments, the plasma torch further comprises an annular permanent magnet arranged radially outwardly of the grounded tube at the open end thereof and configured to produce a magnetic torque on the arc discharge to cause the arc discharge, in use, to rotate around the cathode. The provision of the annular permanent magnet causes the high energy arc to rotate around the cathode, which allows the heat generated in the cathode and grounded tube at the arc location time to be dissipated. This can extends the lifetime of the electrodes as, if the arc were repeatedly incident at the same location on the cathode and grounded tube, these electrodes could overheat and wear out relatively quickly. In accordance with this embodiment, the lifetime of the electrodes is extended, reducing maintenance, and improving the practicality of the two-stage plasma generation system. In other preferred embodiments, however, the permanent magnet can be omitted completely.

The two stages of the plasma may be operated incrementally or independently such that the user may initiate only the non-thermal plasma to treat the wound at a lower energy level, whereas the thermal plasma may be selectively initiated in addition to the non-thermal plasma to treat the wound at a higher energy level. However, it is preferred that the two stages of the plasma are initiated together and injected together, along with the plasma products, through the membrane dressing, because the energy provided by the thermal plasma and/or thermal plasma products helps to convect the non-thermal plasma and/or non-thermal plasma products around the wound thus facilitating faster healing thereof. In use, the injection of plasma and/or plasma products through the membrane dressing into the plasma containment compartment via the input connectors creates a positive pressure therein, and which is maintained in use due to the sealed environment.

In embodiments, the kit of parts in accordance with the aspects and embodiments of the invention described herein further comprises a waste container coupled to an exit connector of the membrane dressing to receive exudate issuing therefrom in use. In embodiments, the waste container comprises a connector to allow the membrane dressing and the waste container to be directly coupled or indirectly coupled through a connector tube to allow fluid communication of the exudate and/or plasma gas through the membrane dressing.

In embodiments, the waste container further comprises a valve which is configured to move from a first position where fluid flow is prevented to a second position where fluid flow is permitted. In use, when the valve is in the second position, the exudate and/or plasma gas flows from the plasma containment compartment to the waste container due to the pressure differential between the positive pressure in the plasma containment area and the lower pressure in the waste container. Removing the exudate from the plasma containment compartment helps to control the level of moisture within the sealed environment, and also helps to prevent maceration of the skin surrounding the wound. In use, once the exudate and/or plasma gas has been removed, or at least partially removed, from the plasma containment compartment the valve may be moved from the second position back to the first position to prevent further fluid flow.

In embodiments, the kit of parts further comprises a control module configured in use to control the plasma generating device to operate in accordance with the aspects and embodiments of the invention described herein. In embodiments, the control module is either part of or provided separately to the plasma generating device. The control module may be implemented using hardware, or hardware and software. There may be provided a data processing module and computer readable medium, optionally non-transitory, comprising instructions which when carried out by the data processing module configure the apparatus to implement the control module.

In use, the control module causes feed gas to be released from the feed gas containers where it is stored under pressure. The control module also causes one or more electrodes in the plasma generating device to cause electrical discharge inside the plasma generating device to ionise the feed gas in the first and/or second cavities.

In accordance with a second aspect of the present invention there is provided an apparatus for treatment of tissue by a contained plasma and/or plasma products, comprising a kit of parts in accordance with the aspects and embodiments of the invention described herein, wherein the membrane dressing is connected directly or indirectly by a connector tube to the plasma generating device to allow conduction of the produced plasma and/or plasma products into the membrane dressing in use.

In embodiments, the electrical power generator unit described herein is coupled to the plasma generating device.

In use, the membrane dressing may be attached via a securing means to the wound, or other tissue requiring treatment, such that the attached membrane dressing provides a sealed environment suitable for containing a fluid and wherein the sealed environment in use has a positive pressure. The securing means may be the adhesive discussed above.

In embodiments, the apparatus further comprises one or more containers of feed gas connected to the plasma generating device, wherein the apparatus is configured such that feed gas is supplied to the first and second cavities to be ionized in use.

In accordance with a third aspect of the present invention there is provided a method of generating and containing a plasma and/or plasma products for use in the treatment of tissue using a kit of parts in accordance with the aspects and embodiments of the invention described herein, the method comprising:
  connecting an opening of the plasma generating device from which plasma and/or plasma products issues to an input connector of the membrane dressing directly or indirectly using a connector tube; and
  operating the plasma generating device to ionize a feed gas to produce a high energy thermal plasma and a low energy non-thermal plasma and plasma products using the plasma generating device that are injected into the membrane dressing.

In embodiments, the method further comprises treating tissue by attaching the membrane dressing over and around tissue requiring treatment, such as a wound.

In embodiments, injecting the plasma and/or plasma products from the plasma generating device into the attached membrane dressing causes, in use, the sealed environment of the attached membrane dressing to have a positive pressure.

In embodiments, the method further comprises uncoupling the plasma generating device from the membrane dressing after a treatment duration or once a pre-determined volume of plasma and/or plasma products has been injected from the plasma generating device into the attached membrane dressing, and retaining the dressing in position around the tissue. The volume of plasma and/or plasma products injected into the membrane dressing can be calculated by integrating the flow rate with respect to time. The concentration of plasma and/or plasma products can then be determined by considering the rate of production of the plasma and/or plasma products versus the rate of degradation of the plasma and/or plasma products within the membrane dressing. In use, the input connector maintains the impermeable seal created by the membrane dressing even after the plasma generating device has been uncoupled.

In embodiments, the method further comprises recoupling the plasma generating device to the attached membrane dressing. In use, if further treatment cycles are required the plasma generating device may be recoupled to the membrane dressing such that further thermal and/or non-thermal plasma and/or related plasma products can be generated and injected through the membrane dressing as described above.

In embodiments, the method further comprises:
  connecting the waste container as described herein to an exit connector of the membrane dressing; and
  moving the valve from the first position to the second position after a pre-determined period of time to allow fluid communication between the attached membrane dressing and the waste container by exploiting a positive pressure within the attached membrane dressing.

In embodiments, the method further comprises moving the valve from the second position to the first position to prevent fluid communication between the attached membrane dressing and the waste container once all, or at least a portion, of the waste fluid has been removed from the attached membrane dressing.

Viewed from another aspect, the present invention provides use of a kit of parts for use in treatment of tissue by a contained plasma and/or plasma products in accordance with the aspects and embodiments of the invention described herein in the surgical treatment of live tissue, optionally for one or more of: wound or burn or ulcer sterilization; cavity sterilization; wound cauterization; wound or burn or ulcer healing.

Viewed from another aspect, the present invention provides use of a kit of parts for use in treatment of tissue by a contained plasma and/or plasma products in accordance with the aspects and embodiments of the invention described herein for use in the surgical treatment of live tissue, optionally for one or more of: wound or burn or ulcer sterilization; cavity sterilization; wound or burn or ulcer healing.

The optional features of the first aspect of the present invention can be incorporated into the second aspect and the third aspect of the present invention and vice versa.

BRIEF DESCRIPTION OF THE DRAWINGS

Aspects of the invention may best be understood by reference to the following description of certain exemplary embodiments together with the accompanying drawings in which.

DETAILED DESCRIPTION

The detailed description set forth below in connection with the appended drawings is intended as a description of presently preferred embodiments of the invention, and is not intended to represent the only forms in which the present invention may be practised. It is to be understood that the same or equivalent functions may be accomplished by different embodiments that are intended to be encompassed within the spirit and scope of the invention. Furthermore, terms "comprises," "comprising," or any other variation thereof, are intended to cover a non-exclusive inclusion, such that apparatuses and method steps that comprises a list of elements or steps does not include only those elements but may include other elements or steps not expressly listed or inherent. An element or step proceeded by "comprises . . . a" does not, without more constraints, preclude the existence of additional identical elements or steps that comprises the element or step.

Figure 1:
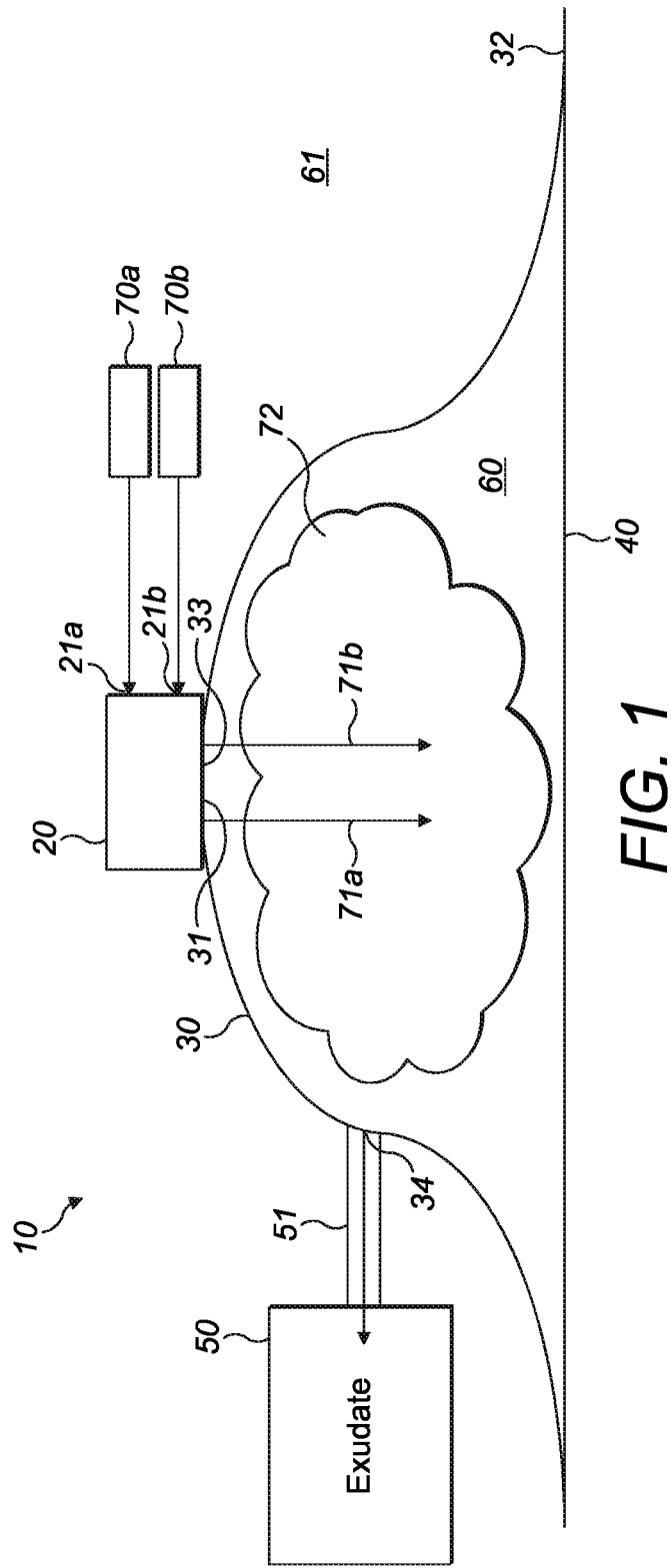
FIG. 1 is a diagram illustrating an apparatus for generating and containing a plasma plume and plasma products for the treatment of tissue according to an embodiment of aspects of the invention.

Referring now to FIG. 1, an apparatus 10 for generating and containing a plasma plume and plasma products in accordance with an embodiment of aspects of the invention includes a plasma generating device 20, herein referred to as a plasma puck, and a membrane dressing 30. The membrane dressing 30 comprises an input connector 31 which allows the plasma puck 20 and the input connector 31 to be directly coupled or indirectly coupled through a connector tube (not shown) to allow fluid communication of the plasma produced by the plasma generating device and plasma products, such as free radicals, through the membrane dressing 30.

The input connector 31 is located at the centre 33 of the membrane dressing 30. In alternative embodiments, the input connector may be located off centre.

As will be described in more detail in FIG. 2, the plasma puck 20 comprises two feed gas inlets 21a and 21b each comprising a feed gas connector (shown in FIG. 2). The apparatus 10 further comprises two containers of feed gas 70a and 70b connected, in use, to the feed gas connectors. In use, there is sealed fluid communication between the containers of feed gas 70a, 70b and the feed gas inlets 21a, 21b. The plasma generated by the plasma puck 20 is a two-stage plasma having a higher energy thermal plasma 71a and a lower energy non-thermal plasma 71b. Optionally, only one of the two stages may be generated. The plasma puck 20 is operated via a control unit (not shown). The thermal and non-thermal plasma 71a, 71b interact in use to produce plasma products, such as free radicals.

The membrane dressing 30 comprises an impermeable and transparent material. The material is also sufficiently rigid that it forms a dome shape, or a blister shape, such that the centre 33 of the membrane dressing 30 extends longitudinally further than an outer portion 32 of the membrane dressing 30, that is the membrane dressing 30 extends away from and is spaced apart from the tissue requiring treatment 40, herein referred to as damaged tissue. The membrane dressing 30 further comprises an outer surface, and a tissue-facing inner surface defining the cavity 60. The outer portion 32 of the inner surface has an adhesive layer, such as an acrylate or compound tincture of benzoin, for attaching and sealing, in use, the membrane dressing 30 over and around the damaged tissue 40, such as a wound or diabetic ulcer. The membrane dressing 30 also, in use, completely seals and isolates a cavity 60 formed between the membrane dressing 30 and the damaged tissue 40 from the surrounding environment 61. The outer portion 32 of the membrane dressing 30 is attached in use to tissue not requiring treatment, such as healthy tissue, with the centre 33 of the membrane dressing 30 sitting over, but not touching, the damaged tissue 40.

The membrane dressing 30 further comprises an exit connector 34 located off centre, longitudinally between the centre 33 and the outer portion 32 of the membrane dressing 30. In use, the input connector 31 and the exit connector 34 respectively maintain the seal of the membrane dressing 30, such that the cavity 60 remains isolated from the surrounding environment 61.

The apparatus 10 further comprises a waste container 50, which itself comprises a connector tube 51. The connector tube 51 attaches to the exit connector 34 of the membrane dressing 30, thus coupling the membrane dressing 30 to the waste container 50. The waste container 50 further comprises a valve (not shown) which is configured to move from a first, or closed, position, where fluid flow between the membrane dressing 30 and the waste container 50 is prevented, to a second, or open, position where fluid flow between the membrane dressing 30 and the waste container 50 is permitted, and then back to the first, or closed, position again.

In use, the membrane dressing 30 is placed over and around damaged tissue 40, such that the centre 33 of the membrane dressing or at least part of the dressing that is dome- or blister-shaped in use is approximately over the centre of the damaged tissue 40. The outer portion 32 of the membrane dressing 30 is then pressed down to ensure the adhesive has formed a complete bond with the surrounding, healthy, tissue, and thus isolating the cavity 60 from the surrounding environment 61. The dome shape of the membrane dressing 30 prevents the membrane dressing 30 from coming into contact with the damaged tissue 40 and helps to prevent aggravation of the damaged tissue 40 if, for example, the membrane dressing 30 has to be removed. Furthermore, the transparent material of the membrane dressing 30 allows the damaged tissue 40 to be seen and monitored without having to touch or remove the membrane dressing 30, thus further mitigating the risk of aggravating the damaged tissue 40. The dimensions of the membrane dressing 30 (such as outer portion 32 circumference and centre 33 longitudinal height) can be varied during manufacture of the membrane dressing 30, such that membrane dressings may be produced to fit over and around damaged tissue spanning a variety of areas.

Once the outer portion 32 of the membrane dressing 30 is secured to the healthy tissue, the plasma puck 20 and the waste container 50 are coupled to the input and exit connectors 31, 34 respectively via the appropriate connectors as described above.

The plasma puck 20 is then caused via the control unit to release feed gas, such as Argon or Nitrogen, from one or both of the containers of feed gas 70a, 70b where they are stored under pressure. The feed gas enters the plasma puck 20 via the feed gas inlets 21a, 21b and flows into ionisation cavities in the plasma puck 20. The control unit then causes one or more electrodes in the plasma puck 20 to cause electrical discharge inside the plasma puck 20. The feed gas inside the plasma puck 20 is then ionised by the discharge and is emitted from the plasma puck 20 as a thermal 71a and/or non-thermal 71b plasma which is then injected into the cavity 60, along with the free radicals, via the input connector 31 of the membrane dressing 30. The thermal 71a and/or non-thermal 71b plasma may be generated for a sustained period of time or may be caused to be emitted in pulses.

The volume of free radicals injected into the cavity 60 is greater than the volume of thermal and non-thermal plasma 71a, 71b injected into the cavity 60.

The injection of plasma and free radicals into the cavity 60 causes a positive pressure within the cavity 60. This positive pressure is maintained due to the seal around the outer portion 32 of the membrane dressing 30, and the input and exit connectors 31, 34 which are arranged to maintain the seal. Within the cavity 60, the higher energy thermal plasma 71a and associated free radicals aids in the convection of the lower energy non-thermal plasma 71b and associated free radicals around the damaged tissue 40. Thus the thermal plasma 71a and the non-thermal plasma 71b and associated free radicals mix together to form a plasma "cloud" 72. The non-thermal plasma 71b generates free radicals such as Nitric Oxide and Ozone, which can help to sterilize and heal the damaged tissue 40. As well as assisting with the convection of the non-thermal plasma 71b, the thermal plasma 71a contributes UV light which can also help to sterilise the damaged tissue 40.

Once a pre-determined volume of thermal and non-thermal plasma and associated free radicals has been injected into the cavity 60 the plasma puck 20 can be uncoupled from the membrane dressing 30. The input connector maintains the seal created by the membrane dressing 30, thus in use preventing any plasma and free radicals from leaking out of the cavity 60 into the surrounding environment 61, and also preventing any gases or bacteria from entering the cavity 60 from the surrounding environment 61, which could otherwise hinder the healing of the damaged tissue 40.

As the damaged tissue 40 heals, it is likely that exudate will be emitted from the wound, and in order to facilitate healing this exudate should ideally be removed from the cavity 60. In use, the valve in the waste container 50 is moved from the closed position to the open position. The positive pressure in the cavity 60, which is higher than the pressure in the waste container 50, causes the exudate, and the plasma "cloud" 72, to be pumped from the cavity 60, through the connector tube 51, and into the waste container 50 where it is collected for disposal. In some embodiments, the used plasma "cloud" may be pumped from the waste container into the plasma puck to be ionised (or re-ionised) to produce further thermal and/or non-thermal plasma and associated free radicals for injection back into the cavity.

Once the exudate has been removed, or at least partially removed, from the cavity 60 along with all or some of the plasma "cloud" 72, the valve is moved from the open position back to the closed position. If the plasma puck 20 was previously uncoupled, it can now be recoupled to the membrane dressing 30, and more thermal and/or non-thermal plasma and associated free radicals can be produced and injected into the cavity 60 by the same method described above.

As the treatment of damaged tissue 40 is non-invasive and may pose minimal health risks and side effects, this method and apparatus could be used by appropriately trained, non-medical personnel in a non-medical setting.

Figure 2A:
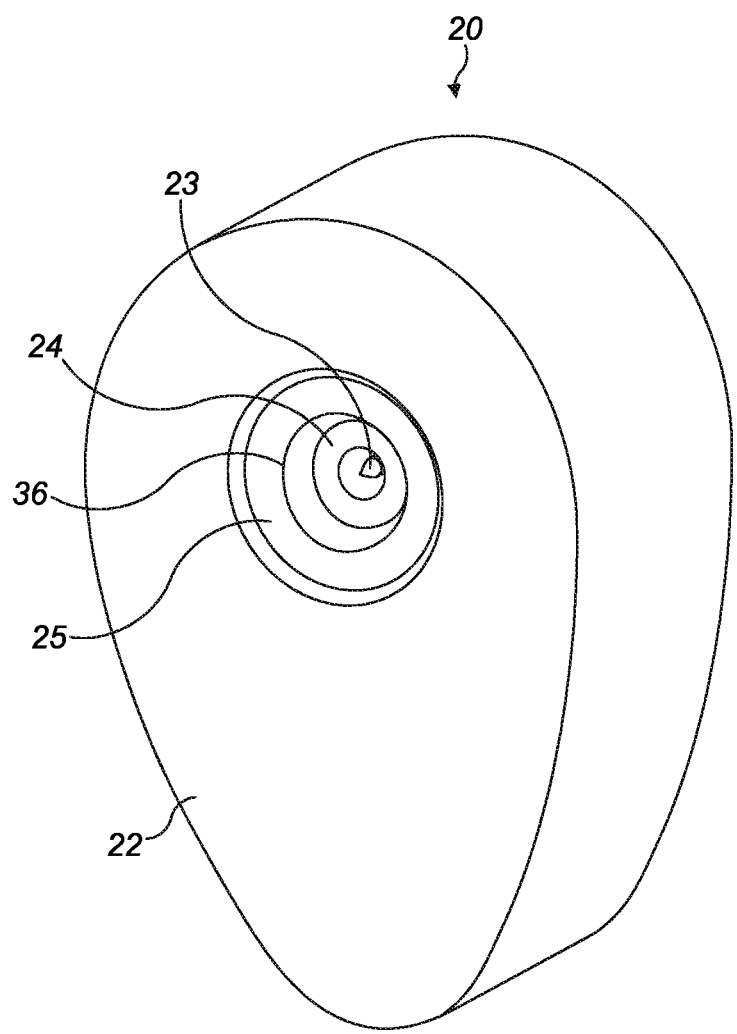
FIG. 2 shows a perspective view A and a sectional views B and C of a plasma generating device for use in the FIG. 1 apparatus.
Figure 2B:
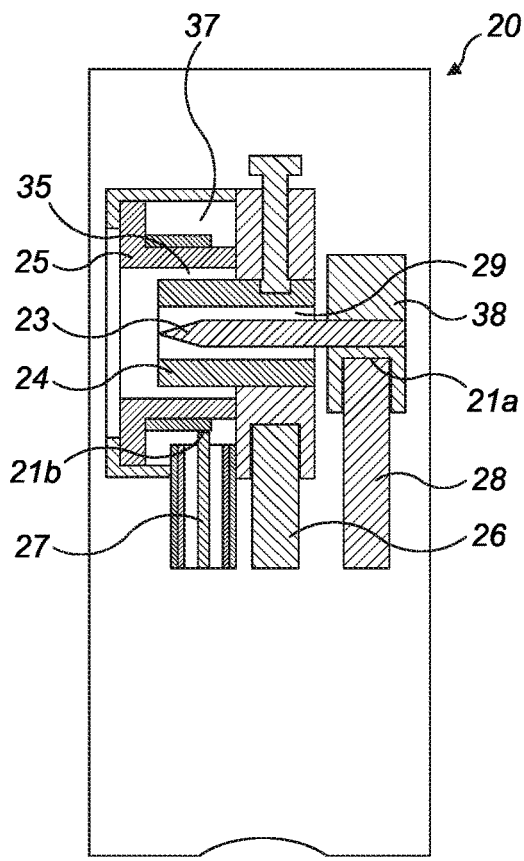
Figure 2C:
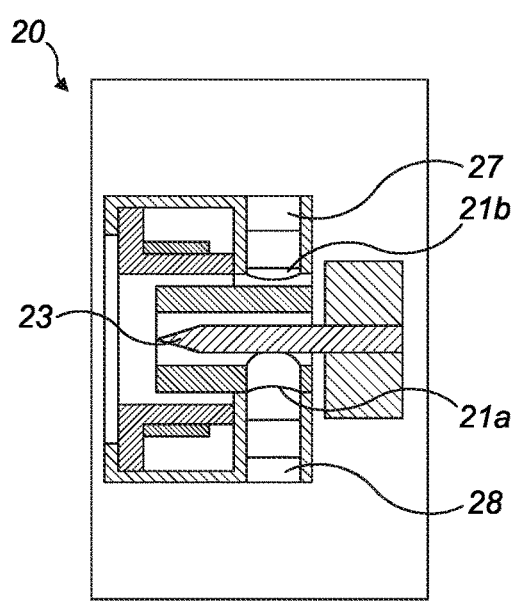

Referring now to FIGS. 2A, 2B and 2C, the plasma puck 20 is shown in more detail, in particular the electrode structure that gives rise to the creation of the thermal 71a and non-thermal 71b plasma in use. The plasma puck 20 includes a housing 22 shaped like a pointed teardrop, and having an opening 36 on one side thereof for emitting the thermal and non-thermal plasma in use. The plasma puck 20 is relatively short in the axis in which the plasma issues from the puck 20, and relatively large in an orthogonal axis.

A cathode rod 23, formed from an emissive material such as tungsten, lanthanated tungsten or thoriated tungsten, is provided and extends along the central axis of the opening 36. The opening 36 is configured to couple in use to the input connector 31, thus allowing in use the plasma and free radicals produced by the plasma puck 20 to be injected into the cavity 60 through the membrane dressing 30 either directly or indirectly via a connector tube.

The cathode rod 23 is supported by and extends from a cathode base 38 to the opening 36 of the plasma puck 20. Arranged coaxially around the cathode rod 23 and spaced apart therefrom, there is provided a grounded stainless steel arc tube 24. A cylindrical annular cavity 29 formed between the rod 23 and the grounded tube 24 is completely sealed except for its front end, where thermal plasma is emitted in use, and the feed gas inlet 21a located on a side thereof. The feed gas inlet 21a is in sealed fluid communication with a feed gas connector 28.

Arranged coaxially around the grounded tube 24 and spaced apart therefrom is a Borosilicate glass or ceramic (Boron Nitride/Alumina) tube 25 that has a dielectric constant of, for example, 4.6 and that acts as a dielectric barrier to a high-voltage copper electrode 37 arranged radially outwardly thereof. A second cylindrical cavity 35 is formed between the grounded tube 24 and the dielectric barrier tube 25 that is completely sealed except for at its front end, where 'cold' non-thermal plasma is emitted in use, and the feed gas inlet 21b located on a side thereof. The feed gas inlet 21b is in sealed fluid communication with a feed gas connector 27. The feed gas inlets 21a, 21b and the feed gas connectors 27, 28 are positioned on the same side of the cathode rod 23.

A grounded plate 26 is provided surrounding the grounded tube 24. The plate 26 is in contact with the housing 22 and acts as the ground reference for the grounded components of the plasma puck 20.

The feed gas connectors 27 and 28 are located at right angles, that is at 90 degrees, to the cathode rod 23 and grounded tube 24, such that the feed gas inlets 21a and 21b provide entry to the cavities 29 and 35 on a side thereof, and not on an end thereof. The cavities 29 and 35 are sealed from each other such that they are not in fluid communication (except via the open front ends) and separate gas supplies are connected through the feed gas connectors 27 and 28 separately. Noble gases such as nitrogen or argon or mixtures thereof may be used as feed gases and different types or compositions of these gases may be fed separately to the two cavities 29 and 35. Alternatively, the same type or composition of gases may be fed separately to both cavities 29 and 35. In some embodiments, the two cavities may be provided side-by-side instead of co-axially. In embodiments, the plasmas from the two cavities may be coupled through the membrane through separate outlets and input connectors.

The geometry of the electrodes and the connectors provides a more compact apparatus which can fit into a flattened handheld device, thus allowing the plasma puck 20 to be more portable and also provide improved patient comfort. Such a portable device could be used outside of a medical setting, such as in the home, and operated by non-medical personnel.

In use, the cathode rod 23 is provided with an electrical power signal sufficient to create an arc between the cathode rod 23 and the grounded tube 24 which is used to generate a 'hot' thermal plasma in the cylindrical annular cavity 29 that is then emitted from the open front end of the cavity 29. To generate the thermal plasma, the cathode 23 is connected to a DC power supply (not shown). The DC power supply consists of a constant supply at ~25V, ~4.2 A DC plus a ballast/ignitor high-voltage pulse circuit to initiate the arc discharge. This DC power supply generates and sustains a voltage and current vs time waveform in which an initial voltage pulse of 200-300V, for example 230V, is applied to the ballast/igniter circuit. This voltage is then increased to 4.5 kV causing the feed gas to break down and an electrical arc to be initiated between the cathode 23 and the grounded tube 24 through the feed gas, before dropping down to around 20-60V DC, preferably 20-30V DC, steady state. The electrical arc provides the heating and ionisation mechanism for generating from the feed gas the highly ionised, higher energy thermal plasma.

The high-voltage electrode 37 is also provided with an electrical power signal which is sufficient to create a dielectric barrier discharge between the dielectric barrier tube 25 and the grounded tube 24 which is used to generate a non-thermal plasma in the cylindrical annular cavity 35 that is then emitted from the open front end of the cavity 35. To generate the lower energy non-thermal plasma, the high-voltage electrode 37 is connected to a high-voltage pulse width modulated (PWM) power supply (not shown) (in other embodiments, an AC power supply may be used rather than a PWM, but a PWM is more efficient and effective in this context). The high voltage PWM power supply consists of a variable frequency PWM power supply providing a PWM voltage signal to high voltage electrode 37 of ~2-8 kV, ~25 mA at a frequency of 23 kHz up to RF for the duration of the discharge. This powers a dielectric barrier discharge between the grounded tube 24 and the dielectric barrier layer tube 25, providing the plasma production mechanism that weekly ionises the feed gas in cavity 35 that is convected downstream under pressure to provide an emission of annular, relatively low energy, non-thermal plasma.

Due to the cavities 29 and 35 being co-axial, the non-thermal plasma is emitted shaped as a halo surrounding the higher energy, thermal plasma. In embodiments where the cavities are side-by-side, then the thermal and non-thermal plasmas will also be emitted side-by-side, parallel to each other.

The electric power is normally provided by an electrical power generator unit. In some embodiments the electric power may be provided by a battery. In such embodiments the battery may be provided separately to or as part of the plasma puck.

The description of the preferred embodiments of the present invention has been presented for purposes of illustration and description, but is not intended to be exhaustive or to limit the invention to the forms disclosed. It will be appreciated by those skilled in the art that changes could be made to the embodiments described above without departing from the broad inventive concept thereof. It is understood, therefore, that this invention is not limited to the particular embodiment disclosed, but covers modifications within the scope of the present invention as defined by the appended claims.

The invention claimed is:

1. A kit of parts for use in treatment of tissue requiring treatment by a contained plasma and/or plasma products, comprising:
a plasma generating device for use with a membrane dressing to be attached to the tissue requiring treatment, comprising:
a first cavity with an opening at one end formed between a high voltage electrode comprising a dielectric barrier material and a grounded electrode such that, in use, a dielectric barrier discharge between the high voltage electrode and grounded electrode ionizes a feed gas to produce at an open end a non-thermal plasma included in the contained plasma and the plasma products;
a second cavity with an opening at one end;
a cathode in the second cavity provided as a central cathode rod, the first cavity formed as a cylinder arranged at least partially around the second cavity and the central cathode rod, the second cavity formed between the grounded electrode and the central cathode rod; and
the membrane dressing for covering the tissue, the membrane dressing comprising:
a sheet of impermeable material configured for forming a plasma containment compartment adjacent the tissue, such that a tissue-facing inner surface of the impermeable material defines a sealed environment which prevents plasma and/or the plasma products from escaping to a surrounding environment; and
one or more input connectors configured to admit the plasma and/or the plasma products through the membrane dressing;
wherein the plasma generating device and the one or more input connectors of the membrane dressing are configured to allow the plasma generating device and the one or more input connectors to be directly coupled or indirectly coupled through a connector tube to allow fluid communication of the plasma and/or the plasma products produced at the opening of the first cavity of the plasma generating device through the membrane dressing to, in use, allow conduction of the produced plasma and/or plasma products into the membrane dressing.

2. A kit of parts for use in treatment of tissue by a contained plasma and/or plasma products as claimed in claim 1, wherein the membrane dressing is at least partly transparent to allow viewing of the tissue during treatment.

3. A kit of parts for use in treatment of tissue by a contained plasma and/or plasma products as claimed in claim 1, wherein the membrane dressing further comprises an outer surface and the tissue-facing inner surface, wherein an outer portion of the inner surface surrounding a plasma containment portion of the inner surface has an adhesive layer for attaching and sealing, in use, the membrane dressing over and around tissue requiring treatment.

4. A kit of parts for use in treatment of tissue by a contained plasma and/or plasma products as claimed in claim 1, wherein at least a plasma containment portion of the membrane dressing is formed to protrude from an outer portion of the membrane dressing as a blister shape, or is configured to form a blister-shape in use, such that a plasma containment portion of the membrane dressing in use extends away from and is spaced apart from the tissue.

5. A kit of parts for use in treatment of tissue by a contained plasma and/or plasma products as claimed in claim 1, wherein the membrane dressing further comprises one or more exit connectors configured to, in use allow exudate and/or plasma gas to issue therethrough through the membrane dressing in use, optionally to a waste container connected thereto and wherein the one or more of the exit connectors is integrated with and optionally cooperates with one or more of the input connectors.

6. A kit of parts for use in treatment of tissue by a contained plasma and/or plasma products as claimed in claim 1, comprising a plurality of membrane dressings having different shapes and sizes for the treatment different sized wounds, the plurality of membrane dressings including the membrane dressing.

7. A kit of parts for use in treatment of tissue by a contained plasma and/or plasma products as claimed in claim 6, wherein:
the grounded electrode of the first and second cavities is provided as a grounded conductive tube arranged around the cathode rod and spaced therefrom to form the second cavity as a cylinder having said opening at one end thereof; and the high voltage electrode of the first cavity is provided around the grounded conductive tube and spaced apart therefrom to form the first cavity having said opening of the first cavity at the one end thereof, the high voltage electrode having the dielectric barrier material at a radially inward-facing surface thereof.

8. A kit of parts for use in treatment of tissue by a contained plasma and/or plasma products as claimed in claim 7, wherein the plasma generating device further comprises at least one feed gas connector for connecting each of the first and second cavities to a feed gas supply and electrical connectors coupled to the connecting the cathode rod, a grounded tube and the high voltage electrode; wherein one or more of the feed gas connectors and/or one or more of the electrical connectors is arranged at a 90 degree angle to the major axis of the cathode rod, the grounded tube and the high voltage electrode and, wherein the plasma generating device is dimensioned generally to be relatively short in the axis in which the plasma issues from the device, and relatively large in an least one orthogonal axis, wherein optionally the plasma generating device is shaped as a puck.

9. A kit of parts for use in treatment of tissue by a contained plasma and/or plasma products as claimed in claim 1, wherein the plasma generating device further comprises at least one connector for coupling, in use, the opening of the plasma generating device through which plasma issues to the one or more input connectors of the membrane dressing or connector tube, or wherein the plasma generating device is formed such that the opening of the plasma generating device through which plasma issues is coupleable to the one or more input connectors of the membrane dressing or connector tube.

10. A kit of parts for use in treatment of tissue by a contained plasma and/or plasma products as claimed in claim 7, wherein the plasma generating device further comprises at least one feed gas inlet opening for each of the first and second cavities; wherein the kit of parts is configured to provide sealed fluid communication between each feed gas inlet and the input connector of the membrane dressing.

11. A kit of parts for use in treatment of tissue by a contained plasma and/or plasma products as claimed in claim 1, wherein the second cavity is formed between the grounded electrode and the cathode such that, in use, an arc discharge between the cathode and the grounded electrode ionizes a feed gas to produce at the open end a thermal plasma and plasma products.

* * * * *

UNITED STATES PATENT AND TRADEMARK OFFICE
CERTIFICATE OF CORRECTION

| | | |
|---|---|---|
| PATENT NO. | : 11,284,499 B2 | Page 1 of 2 |
| APPLICATION NO. | : 16/085403 | |
| DATED | : March 22, 2022 | |
| INVENTOR(S) | : Thomas Frame et al. | |

It is certified that error appears in the above-identified patent and that said Letters Patent is hereby corrected as shown below:

On the Title Page

(57) ABSTRACT
Delete "A kit of parts for use in treatment of tissue by a contained plasma and/or plasma products is disclosed. The kit of parts includes a plasma generating device for use with a membrane dressing attached to tissue requiring treatment. The plasma generating device comprises a first cavity with an opening at one end formed between a grounded electrode and a cathode such that, in use, an arc discharge between the cathode and the grounded electrode ionizes a feed gas to produce at the open end a thermal plasma. Furthermore, the plasma generating device also comprises a second cavity with an opening at one end formed between a high voltage electrode and a grounded electrode such that, in use, a dielectric barrier discharge between the high voltage electrode and grounded electrode ionizes a feed gas to produce at the open end a non-thermal plasma. The membrane dressing is suitable for covering tissue in use, such as a diabetic ulcer, and comprises a sheet of impermeable material configured for forming a plasma containment compartment adjacent to the tissue. The membrane dressing also comprises one or more input connectors configured to admit plasma and/or plasma products through the membrane dressing. The plasma generating device and the one or more input convectors of the membrane dressing are configured to allow the plasma generating device and the input connector to be directly coupled or indirectly coupled through a connector tube to allow fluid communication of the plasma and/or plasma products produced at the openings of the cavities of the plasma generating device through the membrane dressing to, in use, allow conduction of the produced plasma into the membrane dressing. Advantages of such a kit of parts may be that the membrane dressing does not need to be removed to inspect the progress of the wound, nor does it need to be removed and replaced to manage the exudate. Such advantages helps to mitigate the problems of wound aggravation and maceration typically associated with well-known wound dressings, and also helps to encourage and facilitate wound healing."

And insert -- A kit of parts for use in treatment of tissue by a contained plasma and/or plasma products is disclosed. The kit of parts includes a plasma generating device for use Signed and Sealed this
Seventeenth Day of May, 2022

Katherine Kelly Vidal
*Director of the United States Patent and Trademark Office* with a membrane dressing attached to tissue requiring treatment. The plasma generating device comprises a first cavity with an opening at one end formed between a grounded electrode and a cathode such that, in use, an arc discharge between the cathode and the grounded electrode ionizes a feed gas to produce at the open end a thermal plasma. Furthermore, the plasma generating device also comprises a second cavity with an opening at one end formed between a high voltage electrode and a grounded electrode such that, in use, a dielectric barrier discharge between the high voltage electrode and grounded electrode ionizes a feed gas to produce at the open end a non-thermal plasma. The membrane dressing is suitable for covering tissue in use, such as a diabetic ulcer, and comprises a sheet of impermeable material configured for forming a plasma containment compartment adjacent to the tissue. The membrane dressing also comprises one or more input connectors configured to admit plasma and/or plasma products through the membrane dressing. The plasma generating device and the one or more input connectors of the membrane dressing are configured to allow the plasma generating device and the input connector to be directly coupled or indirectly coupled through a connector tube to allow fluid communication of the plasma and/or plasma products produced at the openings of the cavities of the plasma generating device through the membrane dressing to, in use, allow conduction of the produced plasma into the membrane dressing. Advantages of such a kit of parts may be that the membrane dressing does not need to be removed to inspect the progress of the wound, nor does it need to be removed and replaced to manage the exudate. Such advantages helps to mitigate the problems of wound aggravation and maceration typically associated with well-known wound dressings, and also helps to encourage and facilitate wound healing. --